(12) United States Patent
Wieland

(10) Patent No.: US 6,207,376 B1
(45) Date of Patent: Mar. 27, 2001

(54) METHOD OF DETECTION OF POLYMORPHISM AND LOSS OF HETEROZYGOSITY IN A LUNG TUMOR SUPPRESSOR GENE

(75) Inventor: Ilse Wieland, Essen (DE)

(73) Assignee: Roche Diagnostics GmbH, Penzberg (DE)

( * ) Notice: Subject to any disclaimer, the term of this patent is extended or adjusted under 35 U.S.C. 154(b) by 0 days.

(21) Appl. No.: 09/101,373

(22) PCT Filed: Jan. 9, 1997

(86) PCT No.: PCT/EP97/00060

§ 371 Date: Jul. 8, 1998

§ 102(e) Date: Jul. 8, 1998

(87) PCT Pub. No.: WO97/25442

PCT Pub. Date: Jul. 17, 1997

(51) Int. Cl.[7] ............... C12Q 1/68; C12P 19/34; C07H 21/04

(52) U.S. Cl. .................. 435/6; 435/91.1; 536/23.1; 536/24.3

(58) Field of Search .................. 435/6, 91.2; 536/23.1, 536/24.3

(56) References Cited

PUBLICATIONS

Wieland et al, Cancer Research, vol. 54, pp 1775–1774, Mar. 1, 1994.*

Fong et al., Cancer Research, vol. 55, pp 220–223, Jan. 15, 1995.*

* cited by examiner

*Primary Examiner*—W. Gary Jones
*Assistant Examiner*—Jehanne Souaya
(74) *Attorney, Agent, or Firm*—Fulbright & Jaworski,LLP

(57) ABSTRACT

The invention relates to a determination of a polymorphism or less of heterozygosity, by assaying a sample with one or both of SEQ ID NO: 1 and SEQ ID NO: 2. These oligonucleotides facilitate identification of polymorphisms and lack of heterozygosity at chromosomal location 5p15-q21. This region contains a tumor suppressor gene.

8 Claims, No Drawings

SEQUENCE LISTING

<160> NUMBER OF SEQ ID NOS: 2

<210> SEQ ID NO 1
<211> LENGTH: 19
<212> TYPE: DNA
<213> ORGANISM: Homo sapiens

-continued

```
<400> SEQUENCE: 1
gatttgaggg tcatattca                                                    19

<210> SEQ ID NO 2
<211> LENGTH: 18
<212> TYPE: DNA
<213> ORGANISM: Homo sapiens

<400> SEQUENCE: 2
cagtaaatgg  tgcttgga                                                    18
```

METHOD OF DETECTION OF POLYMORPHISM AND LOSS OF HETEROZYGOSITY IN A LUNG TUMOR SUPPRESSOR GENE

FIELD OF THE INVENTION

Allelic deletions on chromosome 5 were analyzed in microdissected human non-small cell lung cancers. Thirty-four primary squamous cell carcinomas, 15 primary adenocarcinomas, and 5 regional lymph node metastases were investigated for loss of heterozygosity (LOH) in chromosomal region 5p15-q21. The sites analyzed included the APC tumor suppressor gene at 5q21, five polymorphic microsatellite markers and the putative tumor suppressor locus del-27, that was assigned to chromosomal region 5p13-12 by FISH analysis. Allelic deletions encompassed larger genomic regions more often in squamous cell carcinomas than in adenocarcinomas. The del-27 and APC regions were identified as two distinct regions with the highest LOH frequencies within 5p15-q21. In squamous cell carcinomas LOH frequencies were 73% at the del-27 and 70% at the APC locus. In adenocarcinomas LOH at the del-27 and APC loci occurred in 38% of the informative cases. Allelic deletion of the APC gene and at the del-27 locus was also detected in the metastases. These results suggest involvement of at least two tumor suppressor genes from chromosome 5 in lung tumorigenesis.

BACKGROUND AND PRIOR ART

Inactivation of tumor suppressor genes appears to be the predominant genetic alteration in many solid tumors. In carcinomas inactivation of known tumor suppressor genes includes deletion of one allele and mutation of the remaining allele or homozygous deletion of both alleles (Rodriguez et al. 1994). To date, tumor suppressor genes p53, Rb1, MTS1 and MTS2 were found to be inactivated in a significant proportion of lung carcinomas (Takahashi et al. 1989; Harbour et al. 1988; Shapiro et al. 1995; Washimi et al. 1995). The MTS1 and MTS2 genes seem to be preferentially lost by homozygous deletion on chromosome 9p (Kamb et al. 1994). The p53 tumor suppressor gene on chromosome 17p and the Rb1 tumor suppressor gene on chromosome 13q are frequently inactivated by allelic deletion combined with mutations in the remaining allele (Kishimoto et al. 1992; Hensel et al. 1990). In non-small cell lung cancer (NSCLC), which is the most common type of lung cancer, allelic deletions detected as loss of heterozygosity (LOH) were reported for multiple chromosomal arms (Shiseki et al. 1994; Sato et al. 1994). This indicates inactivation of several tumor suppressor genes in lung tumorigenesis and progression. Generally, overall LOH incidences were higher in squamous cell carcinomas than in adenocarcinomas (Sato et al. 1994). More extensive analyses to determine homozygous and allelic deletions in NSCLC have been performed on chromosomes 3, 5 and 9. This led to the delineation of a minimal region of loss at 9p21, where the MTS1 and MTS2 genes are located (Merlo et al 1994). At least two regions have been identified on chromosomes 3 and 5 to harbor putative tumor suppressor genes involved in lung tumorigenesis (Yokoyama et al. 1992; Ashion-Rickardt et al. 1991; Wieland and Böhm, 1994).

On chromosome 5q allelic deletion of the known tumor suppressor gene APC at 5q21 was frequently observed in advanced NSCLC and it correlated with a poor prognosis (Hosoe et al. 1994; Fong et al. 1995). In squamous cell carcinomas LOH at 5q21 also correlates with tumor involvement of regional lymph nodes (Fong et al. 1995). Chromosomal region 5q33-35 is considered another target of frequent allelic deletion in advanced NSCLC (Hosoe et al. 1994). There was recently identified a region on chromosome 5 proximal to the APC gene that harbors the putative tumor suppressor locus del-27 (Wieland and Böhm, 1994). The del-27 sequence was isolated by genomic difference cloning, and it is homozygously deleted in a lung carcinoma cell line (Wieland et al. 1992 GeneBank M99171). Here it is shown by fluorescence in situ hybridization (FISH) that the del-27 locus is on chromosomal region 5p13-12. LOH at the del-27 locus occurred frequently in both, squamous cell and adenocarcinomas of the lung. LOH analysis using five polymorphic microsatellite markers in addition to polymorphic sites at the del-27 and APC loci, clearly identified the del-27 and APC region as two distinct regions with the highest LOH frequencies on chromosome 5.

SUMMARY OF THE INVENTION

The invention comprises a method of detection of polymorphism and/or loss of heterzygosity in the lung tumor suppressor gene located in chromosomal region 5p15-q21, its locus being characterized by GeneBank sequence M99171, said method being characterized by mapping human cell specimens using as probes the oligonucleotides 5'GATTTGAGGGTCATATTCA3' (SEQ ID NO: 1) and/or 5'CAGTAAATGGTGCTTGGA3' (SEQ ID NO:2).

Preferably, the probes are used as primers for mapping in a polymerase chain reaction.

DETAILED DESCRIPTION OF PREFERRED EMBODIMENT

Localization of del-27 to Chromosomal Region 5p13-12 by FISH Analysis

Previously, the del-27 sequence was mapped to chromosomal region 5p13-5q14 proximal to the APC tumor suppressor gene at 5q21 using a somatic cell hybrid panel (Wieland and Böhm, 1994). The chromosomal localization of the del-27 sequence obtained by somatic cell hybrid mapping was independently confirmed and refined by FISH. Metaphase spreads from normal human lymphocytes were examined for specific hybridization signals using P1 clones of the del-27 region as hybridization probes. Signals were considered to be specific, if they were detected on each chromatid of a single chromosome. With P1 clone 5234 specific signals were detected in 44 of 50 metaphases examined (88%) and with P1 clone 5235 specific hybridization was observed in 22 of 25 metaphases. In each case the hybridization signals were located in the proximal region of the short arm of chromosome 5p13-12.

LOH in Primary NSCLC

Using the del-27 sequence as a restriction fragment length polymorphism (RFLP) probe we recently showed frequent LOH at this locus in a small sample of squamous cell lung carcinomas (Wieland and Böhm, 1994). Introducing microdissection to specifically isolate tumor cells from tumor biopsies in conjunction with polymerase chain reaction (PCR) enabled us to study LOH on a larger number of lung carcinomas. In this study 53 primary NSCLC consisting of 38 squamous cell carcinomas and 15 adenocarcinomas, and 5 regional lymph node metastases were investigated. Four primary tumor biopsies were not microdissectable because they were heavily infiltrated with leukocytes. LOH at the del-27 locus was determined by PCR based single-strand conformation polymorphism (SSCP) analysis of the del-27 polymorphic HindIII site. LOH at the del-27 polymorphic site was detected in 11 of 15 (73%) primary squamous cell lung carcinomas and in 3 of 8 (38%) primary adenocarcinomas (Table 1). LOH at the polymorphic RsaI site in exon 11 of the APC gene occurred in 14 of 20 (70%) squamous cell carcinomas and in 3 of 8 (38%) adenocarcinomas.

To investigate LOH at additional loci in chromosomal region 5p15-q21 five polymorphic microsatellite markers were included in the LOH analysis. These genomic markers are located in the order D5S630, D5S491, D5S637, D5S626, D5S644 on human chromosome 5 (Gyapay et al. 1994). Marker D5S644 is closely linked to the APC gene on 5q21, and marker D5S637 is located on 5q12 (Wlodarska et al. 1994). Markers D5S637 and D5S626 are both lost in the human/hamster somatic cell hybrid GM11434 that contains a human chromosome 5 with an interstitial deletion of 5q11.2-q13.3. In contrast, markers D5S630 and D5S491 and the del-27 sequence are retained in this somatic cell hybrid and are hence located in the regions flanking this chromosomal deletion (data not shown). Marker D5S630 is most likely located in the distal part of the short arm of chromosome 5 since it is lost in the human/hamster somatic cell hybrids GM11436 and GM11437 that contain a human chromosome 5 with a partial loss of the short arm (data not shown). Of 39 primary lung carcinomas the matching normal tissues were informative at two or more of the analyzed polymorphic sites. LOH frequencies using the polymorphic microsatellites ranged from 38–70% in squamous cell carcinomas and from 0–40% in adenocarcinomas.

There were 14 NSCLC that could be analyzed for LOH at three or more polymorphic loci in region 5p15-5q21. In carcinomas P42, P15 and P19 LOH was confined to the del-27 and flanking loci. In carcinoma P7, LOH affected both the del-27 and the APC region but not the loci flanking del-27. LOH involving all informative loci analyzed occurred in carcinoma P29, whereas LOH in the APC region but not at the del-27 locus occurred in tumors P18, P14, and P24. These results clearly identify the del-27 and the APC region as two distinct regions of allelic deletion on chromosome 5 in both squamous cell and adenocarcinomas of the lung. In squamous cell carcinomas allelic deletions encompassed more often larger genonlic regions as compared with adenocarcinomas in which allelic deletions appeared to be more confined to the relevant loci del-27 and APC.

LOH in NSCLC Metastases

In one of three informative NSCLC cases a lymph node metastasis showed LOH at the del-27 locus but not at the APC locus (P15). LOH of the APC gene and of markers proximal to the APC gene were observed in three of four informative cases with lymph node metastases (P53). Allelic deletions detected in the metastases were already manifest in the corresponding primary tumors. This suggests that the metastases were clonally derived from primary tumor cells.

Discussion

Microdissecting tumor cells from cryostat sections in conjunction with PCR based LOH analysis greatly facilitated this study. When using PCR for LOH analysis, results are easily obscured by contaminating normal stromal cells and infiltrating leukocytes (Wieland et al. 1992; Böhm et al. 1993). This may explain in part the discrepancies between LOH frequencies reported in different studies (Tsuchiya et al. 1992; Wieland and Böhm, 1994; Hosoe et al. 1994: Shiseki et al. 1994; Fong et al. 1995). In fact, we detected LOH at the del-27 locus in one lung tumor (P29) by this assay that we had previously missed by RFLP analysis in Southern blotting experiments (Wieland and Böhm, 1994). In the present study LOH at the del-27 locus on chromosome 5 was determined by PCR based SSCP analysis (Orita et al. 1989). This method detects a single base polymorphism in the previously described polymorphic HindIII site at the del-27 locus and is also sensitive enough to investigate LOH in few isolated tumor cells. To investigate allelic loss flanking the del-27 and APC loci on chromosome 5p13-12 and 5q21, respectively, arbitrarily chosen polymorphic microsatellite markers were used. The main advantage of these simple repeat sequences is that they are highly polymorphic (Gyapay et al. 1994). However, microsatellite sequences may be subject to expansion or contraction in some types of cancer (Loeb, 1994). In NSCLC instabilities of this sort appear to be infrequent on chromosome 5 (Peltomäki et al. 1993), unpublished results). The main disadvantage of microsatellite markers is that PCR amplification often results in staggered bands and care must be taken in interpreting LOH results. If a heterozygous condition in the matching normal cells was not clearly identifiable we evaluated such a case non-informative. This may explain the lower than reported heterozygosity rates (Gyapqy et al. 1994) of our NSCLC cases when using the microsatellite markers. It is also possible that geographical differences in heterozygosity rates exist at these loci.

Squamous cell carcinomas showed higher LOH frequencies at most loci analyzed and they also had more extended allelic deletions than adenocarcinomas of the lung. Widespread loss of 3p and 5q was also found in most small cell lung carcinomas (Ried et al. 1994; Hosoe et al. 1994) and in head and neck squamous cell carcinomas (Ah-See et al. 1994; Speicher et al. 1995). Different patterns of allelic deletion were previously described on chromosome 3p in NSCLC: Squamous cell carcinomas mainly showed monosomy of 3p whereas adenocarcinomas had relatively frequent partial deletions (Yokoyama et al. 1992). This led to the identification of two commonly deleted regions on 3p in adenocarcinomas. The different allelic deletion patterns of squamous cell carcinomas and adenocarcinomas may indicate that different mutational mechanisms are prevalent in the histological subtypes of lung carcinomas. Alternatively, certain genes may be affected at different frequencies in squamous cell carcinomas and adenocarcinomas of the lung as has been shown for the K-ras gene (Bos, 1989) and for E-cadherin (Böhm et al. 1994).

In chromosomal region 5p115-q21 LOH frequencies were highest at the del-27 (5p13-12) and APC (5q21) loci in the analyzed NSCLCs. This suggests the close linkage to two potential tumor suppressor gene loci on chromosome 5 involved in lung tumorigenesis. In previous studies LOH at 5q was found to be more common in advanced than early stage lung carcinomas suggesting that inactivation of a putative tumor suppressor gene on 5q may be a relatively late event in the progression of lung cancer (D'Amico et al. 1992; Hosoe et al. 1994; Fong et al. 1995). Our LOH results at the APC locus appear to confirm this finding: In three of four informative NSCLC cases allelic deletion of the APC gene was detected in the primary tumor and corresponding metastasis. In contrast, no such tendency can be deduced from LOH results at the del-27 locus. LOH of the APC tumor suppressor gene has been reported for some solid tumors other than colorectal carcinomas (D'Amico et al. 1992; Horii et al. 1992; Wieland and Böhm, 1994; Hosoe et al. 1994). However, LOH combined with mutations in the mutation cluster of the APC gene was only infrequently observed in primary lung (Horii et al. 1992), esophageal (Powell et al. 1994) and ovarian cancer (Allan et al. 1994). Whether the APC gene is inactivated in a different manner in these carcinomas than in colorectal carcinomas, or whether mutations occur specifically in the metastatic cells has not been investigated. It is, therefore, not clear whether the APC gene or a closely linked gene is the relevant tumor suppressor gene for these types of cancer.

Cytogenetic alterations involving the short arm of chromosome 5 were reported in non-small cell and small cell lung carcinomas (Wang-Peng et al. 1991; Miura et al. 1992; Testa and Graziano, 1993). Frequent LOH on the short arm of chromosome 5 has not been reported at randomly located polymorphic sites in NSCLC. In contrast to arbitrarily selected markers, the del-27 sequence was isolated by genomic difference cloning to specifically isolate DNA sequences homozygousiy deleted in a lung carcinoma cell line (Wieland et al. 1992). Homozygous deletions in tumor cells are of particular interest when searching for putative tumor suppressor genes because they tend to be much smaller than allelic deletions. In NSCLC relatively frequent homozygous deletions occur on chromosome 9p where the MTS1 and MTS2 genes are located (Washimi et al. 1995). Homozygous deletions in the p53 gene occur in 5–10% of lung carcinomas (Böhm et al. 1993; Harris and Hollstein, 1993). Several homozygous deletions on chromosome 3p in lung carcinoma cell lines have also been reported: A homozygous deletion on chromosome 3p21 involved a chromosomal fragment exhibiting properties of tumor suppression in a hybrid cell assay (Daly et al. 1993). Kok et al. (Kok et al. 1994) reported of a homozygous deletion in a region on chromosome 3p21 frequently affected by LOH. The frequent LOH at the del-27 locus on chromosome 5 together with the homozygous deletion identified in a lung carcinoma cell line (Wieland et al. 1992) suggests that del-27 is located close to a novel putative tumor suppressor gene on the short arm of human chromosome 5.

Materials and Methods
Fluorescence in Situ Hybridization

Two human P1 clones (P1 5234 and P1 5235) containing the del-27 sequence were commercially isolated by Genome Systems, Inc. (St. Louis, Mo., U.S.A.). The entire P1 clones were nick translated using digoxigenin-11-dUTP (Boehringer Mannheim) for FISH analysis and hybridized to normal metaphase spreads in independent experiments. Chromosome preparations were obtained from phytohemagglutinin-stimulated normal peripheral blood lymphocytes cultured for 72 hours. To induce R-banding, the cultures were synchronized with thymidine after 48 hours, incubated overnight at 37° C. and treated with 5-bromodeoxyuridine the next morning, during the final late S-phase, and harvested 6 hours later (Jacky, 1991). Cytogenetic harvests and slide preparations were performed using standard methods. The slides were stored at −80° C. before use. Fluorescence in situ hybridization to metaphase chromosomes was performed as described (Pinkel et al. 1986). Briefly, the slides were denatured for 2 min in 70% formamide/2×SSC (pH 7.0) at 70° C. and dehydrated in ice cold ethanol. The digoxigenin labeled probes (50–100 ng) were dissolved in hybridization mixture (50% formamide, 10% dextran sulfate, 2×SSC plus 10 $\mu$g sheared salmon sperm DNA as carrier), denatured at 75° C. for 5 min and applied to the slides. Hybridization was allowed to proceed overnight in a humid chamber at 37° C. The slides were washed as recommended in the digoxigenin detection kit (Oncoir). Probe detection was accomplished by incubation with the FITC-anti-digoxigenin conjugate (5 $\mu$g/ml, Oncor). The slides were mounted in a modified antifade solution (Lemieux et al. 1992) containing 0.01 $\mu$g/ml propidium iodide as counterstain and examined with a Zeiss Axiophot microscope using appropriate UV-filter combinations. The slides were photographed with an Ektachrome P1600 film (Kodak).

Tumor Specimens

Tumor biopsies from lung cancer patients were collected and processed as described previously (Böhm et al. 1994). From hematoxylin-eosin stained cryostat sections tumor cell islets of 20–50 tumor cells were microdissected under a stereomicroscope (Böhm et al. 1993). Three to five microdissected tumor cell islets containing at least 90% tumor cells were analyzed from different tumor regions. DNA was prepared by proteinase K digestion as described (Wieland et al. 1992; Böhm et al. 1993). DNA from the microdissected tumor cell islets, from normal lung tissue and blood leukocytes was amplified by PCR and further analyzed by SSCP or denaturing polyacrylamide gel electrophoresis.

PCR Amplifications

For mapping analysis of microsatellite markers, DNA of the human/rodent somatic cell hybrid GM11434 [del(5) (5qter>5q13.3::5q11:2>5pter)], GM11436 [der(5) t(4;5)(p15.2;p14.3)] and GM11437 [der (5)t(5;13)(p13;q13)] was obtained from the NIGMS Human Genetic Mutant Cell Repository, Coriell Institute (Camden, N.J., U.S.A.). For PCR amplification of microdissected tumor specimens DNA of 4 to 10 cells was used as template in 50 $\mu$l reactions as described (Wieland et al. 1992; Böhm et al. 1993). Primer sequences 5'GATTTGAGGGTCATATTCA3' (SEQ ID NO:1) and 5'CAGTAAATGGTGCTTGGA3' (SEQ ID NO:2) were selected from the 200 bp sequence flanking the polymorphic HindIII site at the del-27 locus and commercially synthesized (MWG-Biotech, Ebersberg, Germany). PCR cycle conditions were 45 sec at 94° C., 45 sec at 59° C., 1 min at 72° C. for 40 cycles with a final extension step of 7 min at 72° C. SSCP analysis was performed because the polymorphic HindIII site in the amplified 200 bp PCR product is not reliably cleaved by HindIII. Primer sequences for 5p15-q21 microsatellite markers D5S630, D5S491, D5S637, D5S626 and D5S644 were as described (Gyapay et al. 1994). Primer sets D5S637 and D5S644 were included in duplex PCRS. Cycle conditions for all five primer sets were 45 sec at 94° C., 45 sec at 60° C., 1 min at 72° C. for 40 cycles and a final 7 min at 72° C. PCR products were checked on 2–3% agarose gels and further analyzed by denaturing polyacrylamide gel electrophoresis. PCR analysis at the APC locus (a RsaI polymorphic site in exon 11 of the APC gene) was carried out as described (Wieland and Böhm, 1994).

SSCP and Denaturing Polyacrylamide Gel Electrophoresis

For SSCP analysis of the 200 bp PCR product from the del-27 region 2–4 $\mu$l aliquots of the amplification reaction were denatured in 1× loading buffer (10% formamide, 50 mM NaOH, 1 mM EDTA, 1× gel loading buffer III; (Sambrook et al. 1989)) for 2 min at 95° C. and quenched on ice. Samples were electrophoresed on 1× MDE polyacrylamide gels (AT Biochem, Malvern, Pa., U.S.A.) in 1× TBE buffer (90 mM Tris-borate, pH 8, 2 mM EDTA) at constant 6 watt for 15 hours at 20° C. From amplified microsateilites 5–7 $\mu$l PCR aliquotes were denatured and separated by electrophoresis in denaturing 8 M urea/polyacrylamide gels as described (White, 1993). Polyacrylamide gels were silverstained as described (White, 1993).

LIST OF REFERENCES

Ah-See, K. W., Cooke, T. G., Pickford, I. R., Soutar, D. & Balmain, A. (1994). *Cancer Res.*, 54, 1617–1621.

Allan, G. J., Cottrell, S., Trowsdale, J. & Foulkes, W. D. (1994). *Hum. Mulat.*, 3, 283–291.

Ashton-Rickardt, P. G., Wyllie, A. H., Bird, C. C., Dunlop, M. G., Steel, C. M., Morris, R. G., Piris, J., Romanowski, P., Wood, R., White, R. & Nakamura, Y. (1991). *Oncogene*, 6, 1881–1886.

Böhm, M., Totzeck, B., Birchmeier, W. & Wieland, I. (1994). *Clin. Exp. Metastasis,* 12, 55–62.

Böhm, M., Wieland, I. & Totzeck, B. (1993). *Cancer Genet. Cytogenet.,* 65, 83–87.

Bos, J. L. (1989). *Cancer Res.,* 49, 4682–4689.

D'Amico, D., Carbone, D. P., Johnson, B. E., Meltzer, S. J. & Minna, J. D. (1992). *Cancer Res.,* 52, 1996–1999.

Daly, M. C., Xiang, R.-H., Buchhagen, D., Hensel, C. H., Garcia, D. K., Killary, A. M., Minna, J. D. & Naylor, S. L. (1993). *Oncogene,* 8, 1721–1729.

Fong, K. M., Zimmerman, P. V. & Smith, P. J. (1995). *Cancer Res.,* 55, 220–223.

Gyapay, G., Morissette, J., Vignal, A., Dib, C., Fizames, C., Millasseau, P., Marc, S., Bernardi, G., Lathrop, M. & Weissenbach, J. (1994). *Nature Genet.,* 7, 246–339.

Harbour, J. W., Lai, S.-L., Whang-Peng, J., Gazdar, A. F., Minna, J. D. & Kaye, F. J. (1988). *Science,* 241, 353–357.

Harris, C. C. & Holistein, M. (1993). *N. Engl. J. Med.,* 329, 1318–1327.

Hensel, C. H., Hsieh, C.-L., Gazdar, A. F., Johnson, B. E., Sakaguchi, A. Y., Naylor, S.L., Lee, W.-H. & Lee. E.Y.-H.P. (1990). *Cancer Res.,* 50, 3067–3072.

Horii, A., Nakatsuru, S., Miyoshi, Y., Ichii S., Nagase, H., Ando, H., Yanagisawa, A., Tsuchiya, E., Kato, Y. & Nakamura, Y. (1992). *Cancer Res.,* 52, 6696–6698.

Hosoe, S., Ueno, K., Shigedo, Y., Tachibana, I., Osaki, T., Kumagai, T., Tanio, Y., Kawase, I., Nakamura, Y. & Kishimoto, T. (1994). *Cancer Res.,* 54, 1787–1790.

Jacky, P. B. (1991). *The ACT cytogenetics laboratory manual.* Barch, M. J. (ed.), Raven Press: New York, p. 89.

Kamb, A., Gruis, N. A., Weaver-Feldhaus, J., Liu, Q., Harshman, K., Tavtigian, S. V., Stockert, E., Day III, R. S., Johnson, B. E. & Skolnick, M. H. (1994). *Science,* 264, 436–440.

Kishimoto, Y., Murakami, Y., Shiraishi, M., Hayashi, K. & Sekiya, T. (1992). *Cancer Res.,* 52, 4799–4804.

Kok, K., van den Berg, A., Veldhuis, P. M. J. F., van der Veen, A. Y., Franke, M., Schoenmakers, E. F. P. M., Hulsbeek, M. M. F., van der Hout, A. H., De Leij, L., van de Ven, W. & Buys, C. H. C. M. (1994). *Cancer Res.,* 54, 4183–4187.

Lemieux, N., Dutrillaux, B. & Viegas-Péquinot, E. (1992). *Cytogenet. Cell Genet.,* 59, 311–312.

Loeb, L. A. (1994). *Cancer Res.,* 54, 5059–5063.

Merlo, A., Gabrielson, E., Askin, F. & Sidransky, D. (1994). *Cancer Res.,* 54, 640–642.

Miura, I., Graziano, S. L., Cheng, J. Q., Doyle, L. A. & Testa, J. R. (1992). *Cancer Res.,* 52, 1322–1328.

Orita, M., Iwahana, H., Kanazawa, H., Hayashi, K. & Sekiya, T. (1989). *Proc. natl. Acad. Sci. USA,* 86, 2766–2770.

Peltomäki, P., Lothe, R. A., Aaltonen, L. A., Pylkkänen, L., Nyström-Lahti, M., Seruca, R., David, L., Holm, R., Ryberg, D., Haugen, A., Brogger, A., Borresen, A.-L. & de la Chapelle, A. (1993). *Cancer Res.,* 53, 5853–5855.

Pinkel, D., Straume, T. & Gray, J. W. (1986). *Proc. natl. Acad Sci. USA,* 83, 2934–2938.

Powell, S. M., Papadopoulos, N., Kinzier, K. W., Smolinski, K. N. & Meltzer, S. J. (1994). *Gastroenterology,* 107, 1759–1763.

Ried, T., Petersen, I., Holtgreve-Grez, H., Speicher, M. R., Schröck, E., du Manoir, S. & Cremer, T. (1994), *Cancer Res.,* 54, 1801–1806.

Rodriguez, E., Sreekantaiah, C. & Chaganti, R. S. K. (1994). *Cancer Res.,* 54, 3398–3406.

Sambrook, J., Fritsch, E. F. & Maniatis, T. (1989). *Molecular Cloning—A Laboratory Manual.* Cold Spring Harbor Laboratory Press: New York.

Sato, S., Nakamura, Y. & Tsuchiya, E. (1994). *Cancer Res.,* 54, 5652–5655.

Shapiro, G. I., Edwards, C. D., Kobzik, L., Godleski, J., Richards, W., Sugarbaker, D. J. & Rollins, B. J. (1995). *Cancer Res.,* 55, 505–509.

Shiseki, M., Kohno, T., Nishikawa, R., Sameshima, Y., Mizoguchi, H. & Yokota, J. (1994). *Cancer Res.,* 54, 5643–5648.

Speicher, M. R., Howe, C., Crotty, P., du Manoir, S., Costa, J. & Ward, D. C. (1995). *Cancer Res.,* 55, 1010–1013.

Takahashi, T., Nau, M. M., Chiba, I., Birrer, M. J., Rosenberg, R. K., Vinocour, M., Levitt, M., Pass, H., Gazdar, A. F. & Minna, J. D. (1989). *Science,* 246, 491–494.

Testa, J. R. & Graziano, S. L. (1993). Cancer Detect. Prevent., 17, 267–277.

Tsuchiya, E., Nakamura, Y., Weng, S.-Y., Nakagawa, K., Tsuchiya, S., Sugano, H. & Kitagawa, T. (1992). *Cancer Res.,* 52, 2478–2481.

Washimi, O., Nagatake, M., Osada, H., Ueda, R., Koshikawa, T., Seki, T., Takahashi, T. & Takahashi, T. (1995). *Cancer Res.,* 55, 514–517.

Weber, J. L. & May, P. E. (1989). *Am. J Hum. Genet.,* 44, 388–396.

Whang-Peng, J., Knutsen, T., Gazdar, A., Steinberg, S. M., Oie, H., Linnoila, I., Mulshine, J., Nau, M. & Minna, J. D. (1991). *Genes Chrom. Cancer,* 3, 168–188.

White, B. A. (ed). (1993). *PCR Protocols—Current Methods and Applications.* Humana Press: Totowa, N.J.

Wieland, I. & Böhm, M. (1994). *Cancer Res.,* 54, 1772–1774.

Wieland, I., Böhm, M. & Bogatz, S. (1992). *Proc. natl. Acad Sci. USA,* 89, 9705–9709.

Wieland, I., Bolger, G., Asouline, G. & Wigler, M. (1990). *Proc. natl. Acad Sci. USA,* 87, 2720–2724.

Wlodarska, I., De Wolf-Peeters, Ch., Dierick, H., Hilliker, C., Thomas, J., Mecucci, C., Cassiman, J. J. & Van den Berghe, H. (1994). *Cytogenet. Cell Genet.,* 65, 179–183.

Yokoyama, S., Yamakawa, K., Tsuchiya, E., Murata, M., Sakiyanna, S. & Nakamura, Y. (1992). *Cancer Res.,* 52, 873–877.

What is claimed is:

1. A method for detection of a polymorphism or loss of heterozygosity located in chromosome region 5p15-q21, comprising contacting a sample with a first oligonucleotide having the nucleotide sequence of SEQ ID NO: 1, and a second oligonucleotide having the oligonucleotide sequence of SEQ ID NO: 2, and determining hybridization of said oligonucleotides to a nucleic acid molecule in said sample as a determination of a polymorphism or a loss of heterozygosity in said chromosome region.

2. The method of claim 1, wherein said sample is a sample taken from lung tissue of a subject.

3. The method of claim 2, wherein said subject is suspected of having lung cancer.

4. The method of claim 3, wherein said lung cancer is non small cell lung cancer.

5. The method of claim 1, comprising detecting said polymorphism or loss of heterozygosity via polymerase chain reaction.

6. The method of claim 1, wherein said oligonucleotide is labelled.

7. The method of claim 1, wherein said hybridization is indicative of possible presence of lung carcinoma or adenocarcinoma.

8. Composition comprising each of(i) an oligonucleotide, the nucleotide sequence of which consists of SEQ ID NO: 1, and (ii) an oligonucleotide, the nucleotide sequence of which consists of SEQ ID NO: 2.

* * * * *